United States Patent
Walh et al.

(10) Patent No.: US 7,131,725 B2
(45) Date of Patent: Nov. 7, 2006

(54) AUTO-FOCUSSING GLASSES AND METHOD FOR AUTO-FOCUSSING A PAIR OF GLASSES

(75) Inventors: Eberhard Walh, Weilheim (DE); Peter Schnitzer, Heidenheim (DE); Klaus-Peter Schoettle, Oberkochen (DE); Ingo Kohschmieder, Jena (DE)

(73) Assignee: Carl Zeiss Vision GmbH, Aalen (DE)

( * ) Notice: Subject to any disclaimer, the term of this patent is extended or adjusted under 35 U.S.C. 154(b) by 0 days.

(21) Appl. No.: 11/146,164

(22) Filed: Jun. 6, 2005

(65) Prior Publication Data
US 2006/0012747 A1    Jan. 19, 2006

Related U.S. Application Data

(63) Continuation of application No. PCT/EP03/13462, filed on Nov. 28, 2003.

(30) Foreign Application Priority Data
Dec. 6, 2002    (DE) ................................ 102 58 729

(51) Int. Cl.
  *G02C 7/08*    (2006.01)
  *A61B 3/00*    (2006.01)
(52) U.S. Cl. ........................ 351/41; 351/200; 351/205
(58) Field of Classification Search ................. 351/41, 351/158, 200, 205, 211; 349/13
  See application file for complete search history.

(56) References Cited

U.S. PATENT DOCUMENTS

| | | | |
|---|---|---|---|
| 4,181,408 A | 1/1980 | Senders | 351/159 |
| 4,300,818 A | 11/1981 | Schachar | 351/210 |
| 4,756,605 A | 7/1988 | Okada et al. | 349/13 |
| 4,834,528 A | 5/1989 | Howland et al. | 351/211 |
| 4,919,520 A * | 4/1990 | Okada et al. | 349/13 |
| 5,359,444 A | 10/1994 | Piosenka et al. | 349/13 |
| 5,861,936 A | 1/1999 | Sorensen | 351/200 |
| 2004/0056986 A1 * | 3/2004 | Blum et al. | 349/13 |

FOREIGN PATENT DOCUMENTS

DE    197 19 694 A1    11/1998

* cited by examiner

*Primary Examiner*—Huy Mai
(74) *Attorney, Agent, or Firm*—Harness, Dickey & Pierce, P.L.C.

(57) ABSTRACT

A self-focussing spectacle as well as a method for self-focussing a spectacle are proposed. The spectacle comprises at least one spectacle lens of adjustable refracting power, and means for adjusting the refracting power of the spectacle lens as a function of a measured parameter representing a state of accommodation of a corresponding eye of a user of the spectacle. The means measure the refracting power of the eye directly.

14 Claims, 2 Drawing Sheets

AUTO-FOCUSSING GLASSES AND METHOD FOR AUTO-FOCUSSING A PAIR OF GLASSES

CROSS-REFERENCE TO RELATED APPLICATIONS

This application is a continuation of international patent application PCT/EP2003/13462, filed Nov. 28, 2003 and designating the U.S., which was not published under PCT Article 21(2) in English, and claims priority of German patent application DE 102 58 729.9, filed Dec. 6, 2002, which is incorporated herein by reference.

FIELD OF THE INVENTION

The invention, generally, is directed to the field of spectacles.

More specifically, the invention is related to a self-focussing spectacle comprising at least one spectacle lens of adjustable refracting power, and means for adjusting the refracting power of the spectacle lens as a function of a measured parameter representing a state of accommodation of a corresponding eye of a user of the spectacle.

The invention is, further, related to a method for self-focussing a spectacle comprising at least one spectacle lens of adjustable refractive power, and means for adjusting the refractive power of the spectacle lens as a function of a measured parameter representing the state of accommodation of a corresponding eye of a user of the spectacle.

BACKGROUND OF THE INVENTION

A spectacle and a method of the type specified before are known from U.S. Pat. No. 4,300,818.

If a person wishes to fixedly look at objects at different distances with his or her naked eye, it is necessary that the eye accommodates corresponding to the respective distance. The same holds true when the person wears a spectacle having lenses with only one fixed refractive power. However, for persons having only limited accommodation ability, this might present problems because for these persons a sharp vision is only possible over a limited range of distances.

If, however, the person wears spectacles with so-called progressive power lenses having areas of different refractive powers, the person may aim at the respective object with a specific area of the progressive power lens having a refractive power that just matches the distance to that object, and he or she may do so by altering the direction of sight or the head orientation, respectively. The eye must then not accommodate because there is already provided for it a matching spectacle lens area for each distance.

Moreover, one has also already suggested so-called self-focussing or adaptive spectacles having lenses, the refractive power of which may be adjusted as a whole by remote control. A user may then aim at objects at different distances without the need of selecting a matching spectacle lens area. No accommodation takes place, either.

Such spectacles require lenses that may be adjusted in their refractive power by means of electrical signals.

U.S. Pat. No. 4,756,605 discloses such a spectacle, the lenses of which being configured as liquid crystal devices (LCD). By means of a potentiometer located at the spectacle bridge the refractive power of the right and of the left spectacle lens of this prior art spectacle may be adjusted manually and individually.

The drawback of this prior art spectacle is that the refractive power of both spectacle lenses must be adjusted separately and manually in a cumbersome manner. If the direction of sight is altered, the focussing of the spectacle lenses may be effected only with a certain delay.

U.S. Pat. No. 5,359,444 discloses a self-focussing spectacle avoiding the afore-discussed drawbacks. This prior art spectacle is provided with two infrared range finders at its frame measuring the distance to the aimed object. The refractive power of the two spectacle lenses is then automatically adjusted as a function of that distance.

Although this prior art spectacle avoids the problem of manual adjustment, this approach in practice still has significant disadvantages, in particular when the range finder is unable to exactly determine which object within the field of view shall be aimed at. This is the case, for example, when someone looks outside through a nearby window and the range finder cannot discern whether the plane defined by the window frame or, for example, a landscape shall be aimed at that is in view through the window. The same applies when someone looks by an edge of a house or attempts to aim at a movable object in front of a stationary background.

Another self-focussing spectacle is described in U.S. Pat. No. 4,300,818 mentioned at the outset. This prior art spectacle, for adjusting the refractive power of the spectacle lenses, makes a measurement on the user's eyes for measuring a parameter representing the state of accommodation of the eye. In this prior art spectacle, the so-called angle of convergence is measured, i.e. the angle enclosed between the axes of the two eyes. For that purpose, two light beams are directed on the user's eyeballs, and one detects whether the corresponding point of reflection is located on the bright sclera or on the dark cornea of the eye. The refractive power of the spectacle lenses is then adjusted as a function of the angle of convergence so determined.

Although this prior art self-focussing spectacle takes into account where the user wants to look at, it still has practical disadvantages.

In this prior art self-focussing spectacle the determination of the angle of convergence namely makes it mandatory to measure both eyes of the user. Therefore, it is not possible to individually take into account the refractive power of each eye.

Moreover, this prior art spectacle assumes that there exists a constant relation between the accommodation of the eye and the angle of convergence, which must not at all be always the case in practice. Moreover, the measurement is not unequivocal when the user moves his or her eyes in a vertical direction. Moreover, instabilities within the closed loop control may come up, i.e. oscillations may occur when the setting of the refractive power of the spectacle lens and the adjustment of the optical axes of the user's eyes counteract with each other.

A substantial disadvantage of the prior art self-focussing spectacles, however, is that with such spectacles the adjustment of the refractive power of the spectacle lenses is effected to an extent that the user himself or herself does not need to accommodate any more at all. As a consequence, for persons having a reduced, but still to a certain extent existing ability of accommodating, such ability to accommodate with one's own eyes grows weary and becomes unlearned within a very short period of time.

It is, therefore, an object underlying the invention to provide a spectacle and a method of the type specified at the outset such that the afore-explained disadvantages are avoided.

In particular a spectacle and a method, respectively, shall be provided that are safe in operation and insusceptible to failures. Moreover the still existing ability of a user to accommodate his or her eyes shall be trained continuously and, therefore shall not go lost.

In a spectacle of the type specified at the outset, this object is achieved in that the means measure the refracting power of the eye directly.

In a method of the type specified at the outset, this object is achieved in that the refractive power of at least one eye is measured by the means directly.

The object underlying the invention is, thus, entirely solved.

If, namely, the refractive power of the user's eye is measured directly, one has a direct measure for the required compensating refractive power of the corresponding spectacle lens. Unlike in the case of a measurement of the angle of convergence one has not the need to fall back to an auxiliary interrelation of two ophthalmological quantities, because the only interesting quantity, namely the refractive power, is measured and compared directly.

In a preferred embodiment of the invention, a least one light emitter directed towards the eye, and a light receiver associated to the light emitter and adapted to receive a light signal reflected by the eye are provided, and the means adjust the refracting power of the spectacle lens as a function of the reflected light signal.

This measure has the advantage that the refractive power of the eye may be measured directly with the help of proven methods. Preferably, this was effected with non-visible light, in particular with infrared light.

In a preferred improvement of this embodiment of the invention the means measure the refractive power of the at least one eye by directing a light beam into the eye. This is preferably done such that the distance between a cornea and a front surface of a lens of the eye are measured.

This measure has the advantage that the refractive power of the eye may be determined in a particularly simple manner. However, other methods may likewise be used within the context of the present invention.

In a further preferred embodiment of the inventive spectacle, the means measure the refractive power for each eye individually, and individually adjust the refractive power of the spectacle lens corresponding to the respective eye.

This measure, in contrast to the above-referred prior art has the advantage that an individual adjustment of the refractive power of the corresponding spectacle lens is possible for each eye.

In a particularly preferred embodiment of a spectacle according to the present invention the means adjust the refractive power of the at least one spectacle lens only after a predetermined threshold value of the refractive power of the corresponding eye has been exceeded.

This measure has the advantage that the natural ability of accommodation is continued to be trained, i.e. within its limits that may be restricted. This is because as long as the user's eye is urged to just accommodate within those limits as can still be effected naturally, the spectacle according to the invention does not interfere. Only when the predetermined threshold value of the eye is reached, from where on a natural accommodation is impossible for the respective user, the control of the spectacle according to the present invention is activated.

The same holds true, mutatis mutandis, for the embodiments of the methods according to the present invention.

For the last mentioned embodiment it is particularly preferred when the limit of the refractive power range of the at least one eye that can be naturally adjusted by the user, is measured first and the threshold value is set as a predetermined fraction of the limit, preferably as between 80 and 98% of the limit.

This measure has the advantage that an activation threshold for the control according to the present invention may be preset in a predetermined manner without the need of constantly measuring the natural limit of the user's ability to accommodate.

Further advantages will become apparent from the description and the enclosed drawings.

It goes without saying that the features mentioned before and those that will be mentioned hereinafter may not only be used in the particularly given combination but also in other combinations or alone without leaving the scope of the present invention.

An embodiment of the invention is shown in the drawing and will be explained in further detail within the subsequent description.

Figure 1:
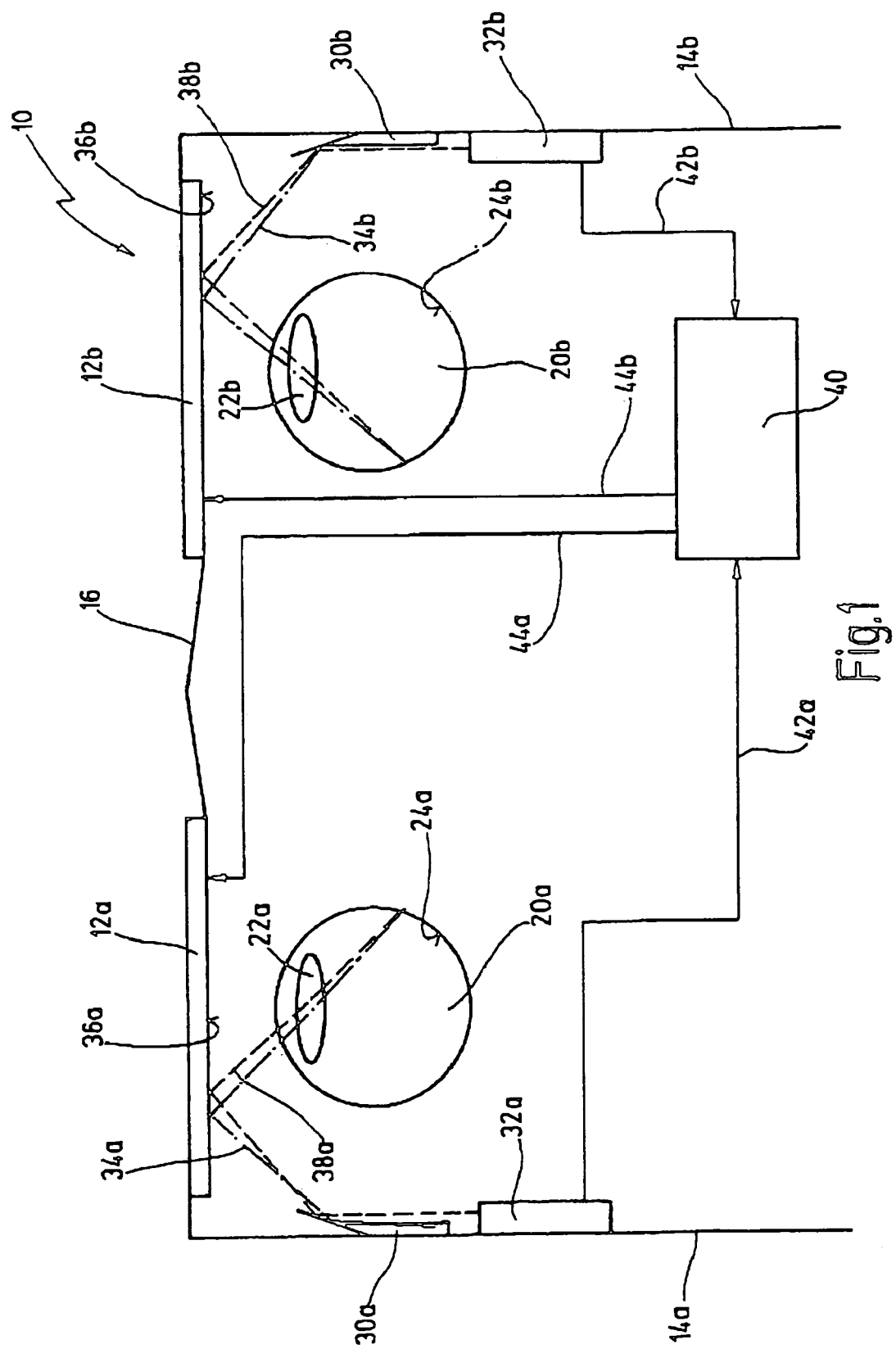
FIG. 1 shows an extremely schematic top plan view of an embodiment of a self-focussing spectacle according to the present invention.

In FIG. 1 reference numeral 10 as a whole indicates an embodiment of a self-focussing spectacle according to the present invention. Spectacle 10 is provided with spectacle lenses 12a, 12b which are adapted to be adjusted in their refractive power by remote control. Such spectacle lenses are conventionally configured as liquid crystal elements (LCD), as, e.g., is disclosed in U.S. Pat. Nos. 4,919,520, 5,066,301 and 4,601,545.

Spectacle 10, further, on its lateral sides has side pieces 14a, 14b as well as a bridge 16 bridging spectacle lenses 12a, 12b.

Eyes of a user of spectacle 10 are indicated in FIG. 1 at 20a, 20b. Within eyes 20a, 20b, eye lenses 22a, 22b and retinas 24a, 24b are shown each.

Light emitters 30a, 30b, emitting, preferably, non-visible light, in particular infrared light, are arranged on side pieces 14a, 14b. Moreover, light receivers 32a, 32b, preferably cameras, are likewise arranged on side pieces 14a, 14b.

Light emitters 30a, 30b emit light beams 34a, 34b. Light beams 34a, 34b are reflected at rear surfaces 36a, 36b of spectacle lenses 12a, 12b and are directed to eye lenses 22a, 22b onto retinas 24a, 24b of eyes 20a, 20b. The reflected light beams 38a, 38b are received by light receivers 32a, 32b. Signals, derived therefrom are fed to a control unit 40 via control lines 42a, 42b. Control unit 40 generates control signals from these input signals and feeds the control signals to spectacle lenses 12a, 12b via further control lines 44a, 44b.

Figure 2:
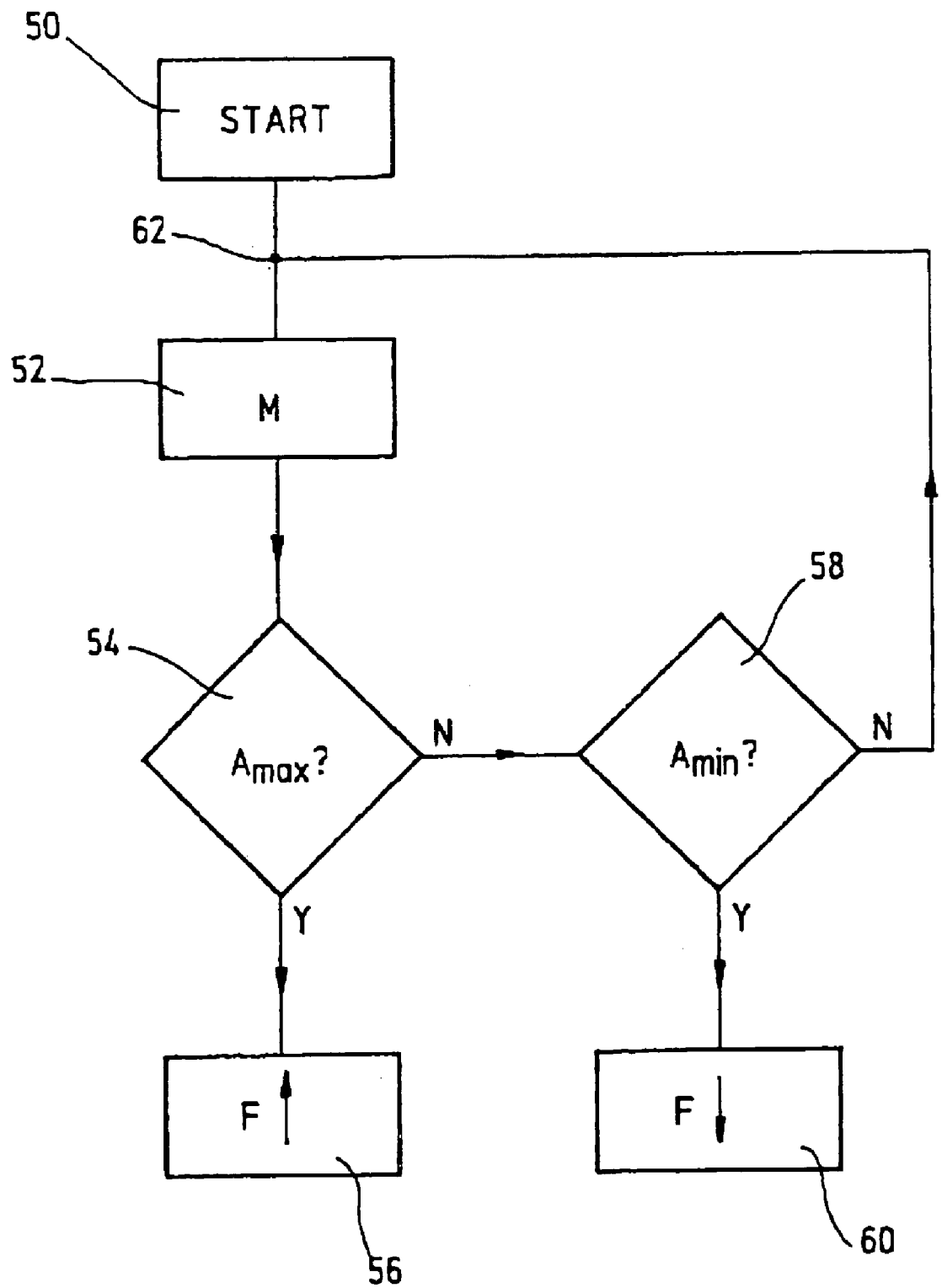
FIG. 2 shows a schematic flow chart for explaining the operation of the spectacle of FIG. 1.

The operation of spectacle 10 of FIG. 1 shall now be further explained with the help of the flow chart shown in FIG. 2.

In a block 50 it is indicated that the method according to the present invention shall be started first.

In a block 52 a measurement M of its refractive power is now executed individually for each eye 20a, 20b, by accordingly evaluating the above-mentioned light beams 34a, 34b and 38a, 38b, respectively.

Such methods of evaluating and measuring the refractive power of an eye lens are known in the prior art. It is, for example, possible to measure the distance between the cornea and a front surface of eye lens 22a, 22b. Moreover, refraction measurements may be executed as are, for example, described in U.S. Pat. Nos. 4,834,528 as well as in German disclosure document DE 197 19 694 A1.

The signal measured in block 52 and corresponding to the actual refractive power of eye 20a and 20b, respectively, may now be directly used for adjusting the refractive power of the respective corresponding spectacle lens 12a and 12b, respectively.

However, the invention prefers another approach in which one examines first whether a maximum value of accommodation $A_{max}$ and a minimum value $A_{min}$ of the respective eye 20a, 20b, respectively, has been reached.

In the flow chart of FIG. 2 it is first examined in a block 54 whether the maximum value $A_{max}$ or a certain fraction thereof, e.g. within the range of between 80 and 98% of the maximum value $A_{max}$, has been reached. Only if that is the case, the refractive power of the corresponding spectacle lens 12a and 12b, respectively, is increased in a block 56.

If the maximum value $A_{max}$ was not reached, it is examined within a block 58 whether a minimum value $A_{min}$ was reached. If that is the case, the refractive power of the corresponding spectacle lens 12 and 12b, respectively, is decreased in a block 60. If the minimum value $A_{min}$ was not reached either, this is a measure indicating that the refractive power of the eye 20a and 20b, respectively, is still within the range which the user may adjust naturally. In that case the control according to the present invention remains inactive so that the user may further use and train the ability of his or her eyes 20a and 20b, respectively, to accommodate naturally. The method in such a situation at a point 62 returns to the start position for then again make a measurement M in block 52 because the user in the meantime might have changed the direction of sight and, simultaneously, the aiming at a specific object.

The flow chart shown in FIG. 2 may be executed in a fast repetition rate in order to be able to quickly follow changes in requirements.

The invention claimed is:

1. A self-focussing spectacle comprising:
   at least one spectacle lens of adjustable refracting power;
   means for directly measuring a refracting power of an eye of a user of said spectacle; and
   means for adjusting said refracting power of said at least one spectacle lens as a function of said measured refracting power of said eye.

2. The spectacle of claim 1, wherein said eye corresponds to said at least one spectacle lens.

3. The spectacle of claim 2, wherein at least one light emitter directed towards said eye and a light receiver associated to said light emitter and adapted to receive a light signal reflected by said eye are provided, said adjusting means adjusting said refracting power of said spectacle lens as a function of said reflected light signal.

4. The spectacle of claim 3, wherein said measuring means measures said refracting power of said eye by directing a light beam into said eye.

5. The spectacle of claim 4, wherein said measuring means measures a distance between a cornea and a front surface of a lens of said eye.

6. The spectacle of claim 1, wherein said adjusting means adjusts said refracting power of said at least one spectacle lens only after a predetermined threshold value of said refracting power of said eye has been exceeded.

7. A self-focussing spectacle comprising:
   two spectacle lenses of adjustable refracting power;
   means for directly and individually measuring a refracting power of two eyes of a user of said spectacle, said two eyes corresponding to said two spectacle lenses; and
   means for adjusting said refracting power of each of said two spectacle lenses individually as a function of said individually measured refracting power of said corresponding eye.

8. A method for self-focussing a spectacle having at least one spectacle lens of adjustable refracting power, the method comprising the steps of:
   directly measuring a refracting power of an eye of a user of said spectacle; and
   adjusting said refracting power of said at least one spectacle lens as a function of said measured refracting power of said eye.

9. The method of claim 8, wherein said eye corresponds to said at least one spectacle lens.

10. The method of claim 9, wherein said refracting power is measured by measuring a distance between a cornea and a front surface of a lens of said eye.

11. The method of claim 9, wherein said refracting power of said at least one spectacle lens is adjusted only after a predetermined threshold value of said refracting power of said eye has been exceeded.

12. The method of claim 11, further including the steps of measuring a limit of refracting power range of said eye that can be naturally adjusted by said user, and setting said threshold value as a predetermined fraction of said limit.

13. The method of claim 12, wherein said fraction is between 80 and 98% of said limit.

14. A method for self-focussing a spectacle having two spectacle lenses of adjustable refracting power, the method comprising the steps of:
   directly and individually measuring a refracting power of two eyes of a user of said spectacle, said two eyes corresponding to said two spectacle lenses; and
   individually adjusting said refracting power of each of said two spectacle lenses as a function of said individually measured refracting power of said corresponding eye.

* * * * *

UNITED STATES PATENT AND TRADEMARK OFFICE
CERTIFICATE OF CORRECTION

| | | |
|---|---|---|
| PATENT NO. | : 7,131,725 B2 | Page 1 of 1 |
| APPLICATION NO. | : 11/146164 | |
| DATED | : November 7, 2006 | |
| INVENTOR(S) | : Eberhard Wahl et al. | |

It is certified that error appears in the above-identified patent and that said Letters Patent is hereby corrected as shown below:

Title Page,
Items [12] and [75] Inventors, "Eberhard Walh" should be -- Eberhard Wahl --.

Signed and Sealed this

Eighth Day of May, 2007

JON W. DUDAS
*Director of the United States Patent and Trademark Office*